(12) United States Patent
McGaffigan

(10) Patent No.: US 7,326,202 B2
(45) Date of Patent: Feb. 5, 2008

(54) TUBULAR RESISTANCE HEATER WITH ELECTRICALLY INSULATING HIGH THERMAL CONDUCTIVITY CORE FOR USE IN A TISSUE WELDING DEVICE

(75) Inventor: Thomas H. McGaffigan, Saratoga, CA (US)

(73) Assignee: Starion Instruments Corporation, Sunnyvale, CA (US)

( * ) Notice: Subject to any disclaimer, the term of this patent is extended or adjusted under 35 U.S.C. 154(b) by 87 days.

(21) Appl. No.: 10/383,858

(22) Filed: Mar. 7, 2003

(65) Prior Publication Data

US 2004/0176756 A1   Sep. 9, 2004

(51) Int. Cl.
 A61B 18/04    (2006.01)
(52) U.S. Cl. .............................. 606/29; 606/27; 606/28
(58) Field of Classification Search .................. 606/41, 606/45–52, 27–29; 607/98; 392/438–439; 29/611–613; 338/306–309
See application file for complete search history.

(56) References Cited

U.S. PATENT DOCUMENTS

| | | |
|---|---|---|
| 1,422,826 A | 7/1922 | Brown |
| 2,012,937 A | 9/1935 | Beuoy |
| 2,866,062 A | 12/1958 | Fisher |
| 3,898,431 A | 8/1975 | House et al. |
| 3,980,861 A | 9/1976 | Fukunaga |
| 4,783,586 A | 11/1988 | Takeda |
| 4,950,873 A | 8/1990 | Shida et al. |
| 5,453,599 A | 9/1995 | Hall, Jr. |
| 5,665,262 A | 9/1997 | Hajaligol et al. |
| 5,875,283 A | 2/1999 | Yane et al. |
| 6,132,429 A * | 10/2000 | Baker ........................ 606/50 |
| 6,313,439 B1 | 11/2001 | Fischbach et al. |
| 6,410,886 B1 | 6/2002 | Julien |
| 6,626,901 B1 * | 9/2003 | Treat et al. .................. 606/29 |
| 2002/0096512 A1 * | 7/2002 | Abbott et al. ............... 219/543 |
| 2003/0144652 A1 * | 7/2003 | Baker et al. ................ 606/28 |

FOREIGN PATENT DOCUMENTS

WO    WO-98/38935    *   9/1998

* cited by examiner

Primary Examiner—Lee S. Cohen
(74) Attorney, Agent, or Firm—Gordon & Rees, LLP

(57) ABSTRACT

A resistance heater for use in a tissue sealing and cutting device, including a tubular heating element adapted to conduct current therethrough; and a thermally conductive electrical insulator disposed within the tubular heating element.

30 Claims, 3 Drawing Sheets

TUBULAR RESISTANCE HEATER WITH ELECTRICALLY INSULATING HIGH THERMAL CONDUCTIVITY CORE FOR USE IN A TISSUE WELDING DEVICE

TECHNICAL FIELD

The present invention relates generally to tissue sealing and cutting systems, and in particular to thermal welding tissue sealing and cutting systems.

BACKGROUND OF THE INVENTION

Tissue welding devices typically comprise a pair of tweezers, jaws or forceps that grasp onto and hold tissue therebetween. Tissue welding devices may operate with a heating element in contact with the tissue, or with an ultrasonic heater that employs frictional heating of the tissue, or with a bipolar electrode heating system that passes current through the tissue such that the tissue is heated by virtue of its own resistance. Tissue welding devices are used to heat the tissue to temperatures such that the tissue is either "cut" or "sealed", as follows.

When tissue is heated in excess of 100 degrees Celsius, the tissue disposed between the tweezers, jaws or forceps will be broken down and is thus, "cut". However, when the tissue is heated to temperatures between 50 to 90 degrees Celsius, the tissue will instead simply "seal" or "weld" to adjacent tissue.

An example of a tissue welding device is found in Published PCT patent applications WO 98/38935 and WO 01/12090, and is also found in the TLS™ Thermal Ligating Shears and the Cautery Forceps devices sold by Starion Instruments Corporation of Saratoga, Calif. An advantage of the Starion devices are that they can be used to simultaneously cut and seal the ends of a blood vessel.

In the Starion tissue welding devices, a resistance wire heating element is a disposed on the surface of one of two opposing working surfaces of a pair of tweezers or forceps. The blood vessel to be sealed or cut is held between the opposing working surfaces of the device, and the resistance wire is heated. The portion of the blood vessel that is immediately adjacent to the resistance wire will be heated to temperatures in excess of 100 degrees Celsius (thereby "cutting" through the blood vessel at this location). When heated to this temperature, the tissue protein structure breaks down. On either side of this "cut zone", the tissue will only be heated to temperatures between 50 to 90 degrees Celsius. When heated to this lower temperature, the tissue proteins become denatured and thus bond together. Therefore, when accompanied by mechanical pressure caused by gently squeezing the two opposing working surfaces together, the tissue will "seal" together, thus forming a "seal zone" on either side of the central "cut zone". In these two seal zones, the ends of the blood vessel will be sealed shut.

When heating tissue with a resistance wire positioned in direct contact with the tissue, the temperature that the tissue is actually heated to is dependent upon the watt density of the heater. Moreover, high watt densities are required in order to achieve high local temperatures, especially into the "cut" temperature range (in excess of 100 degrees Celsius). Because of the limitations of small, lightweight DC power supplies, a small diameter resistance wire is required to achieve sufficiently high resistance and resulting watt densities, especially for tissue cutting temperatures.

A disadvantage of using a small diameter resistance wire for tissue sealing and cutting is that the contact area between the wire and the surrounding tissue is small. Thus, heat from the wire is only applied to a small area of the tissue. It would instead be desirable to increase the area of tissue to which heating is directly applied. This would be especially beneficial, for example, when sealing the end of a blood vessel since the creation of a larger "seal zone" at the end of the blood vessel would help ensure the blood vessel remains sealed.

Unfortunately, simply increasing the contact area between the resistance wire and the surrounding tissue by increasing the diameter of the resistance wire would result in decreasing the resistance and the watt density of the wire, thus significantly limiting the wire's tissue heating ability. To counteract this decreased watt density problem, it would therefore be necessary to increase the power applied to the wire. Unfortunately, such increased power levels tend to exceed the limits of existing small, lightweight DC power supplies. What is instead desired is a system in which the surface area (where the heater contacts surrounding tissue) is increased, but without changing the resistance or compromising watt density while working within the limitations of existing small power supplies.

In other non-medical resistance heater systems, the heating element comprises a resistance wire heater that is surrounded by a high resistance, electrically insulating, high thermal conductivity material that is in turn surrounded by a protective outer metal sleeve. In such systems, current is passed through the central resistance wire which is thus heated. The heat is then conducted outwardly through the high thermal conductivity material and the outer metal sleeve. In such systems, current is not passed through the outer metal sleeve. A disadvantage of such systems is that they are slow to heat up and slow to cool down.

SUMMARY OF THE INVENTION

In accordance with a first aspect of the present invention, a novel resistance heater for use in a tissue sealing and cutting (e.g. thermal tissue welding) device is provided. Specifically, the present invention provides a resistance heater for use in a tissue sealing and cutting device, including: a tubular heating element adapted to conduct current therethrough; and a thermally conductive electrical insulator disposed within the tubular heating element.

The present novel resistance heater design has many different advantages. For example, the present resistance heater may have a larger diameter than a comparable wire resister, without sacrificing watt density or requiring a larger power supply. An advantage of having a larger diameter is that the surface contact area with the surrounding tissue will be larger. Such a larger surface contact area will result in a larger tissue "treatment" (i.e.: sealing and cutting) area. It is desirable to have a large surface area to ensure that the cutting is performed thermally, not mechanically. In accordance with the present invention, therefore, the surface area of the present heating element can be made larger than that of a comparable solid wire heating element employing the same power to the heater.

Morever, the tubular shape of the present heating element can be used to maintain as high a watt density as that achieved with a smaller diameter solid resistance wire heater. Specifically, by making the thickness of the heating element tube very thin, the effective electrical cross section of the heater remains small, thus maintaining or increasing its resistance (thereby maintaining high watt densities).

Advantages of having the inner core of the heater made of a thermally conductive electrical insulator include: the heater can be rugged, easily bent, and have increased longitudinal and transverse thermal conductivity. In addition, a further advantage of the present design is that the heating element may achieve uniform temperatures both along its length and across its thickness (despite varying thermal loads along its length). Specifically, the high thermal conductivity of the core promotes such uniform temperatures.

In optional preferred aspects, the present invention may further comprise a temperature sensing element disposed within the thermally conductive electrical insulator. Such temperature sensing element may be any suitable temperature sensing element, including, but not limited to, a thermocouple, a thermistor, a PTC element or an NTC element.

In accordance with a second aspect of the present invention, a novel thermal tissue welding system for sealing and cutting tissue is provided. This thermal tissue welding system incorporates the present novel resistance heater, and the overall system itself may comprise a pair of tweezers or a pair of forceps, or other devices. In preferred embodiments, the present invention provides a system for sealing and cutting tissue, including: a body comprising a pair of opposing working surfaces that may be moved together and apart; and a resistance heater disposed on at least one of the working surfaces, wherein the resistance heater comprises a tubular heating element adapted to conduct current therethrough and a thermally conductive electrical insulator disposed within the tubular heating element.

In optional preferred aspects, the body comprising a pair of opposing working surfaces is a pair of tweezers. In alternate optional preferred aspects, the body comprising a pair of opposing working surfaces is a pair of forceps. Other suitable tissue welding devices may also be used, all keeping within the scope of the present invention.

In accordance with a third aspect of the present invention, a novel method of sealing and cutting tissue with a thermal tissue welding device incorporating the present novel resistance heater is provided. Specifically, the present invention provides a method of cutting or sealing tissue with a thermal tissue welding device, including: grasping the tissue between two opposing working surfaces of the thermal tissue welding device, wherein a resistance heater is disposed on at least one of the working surfaces, and wherein the resistance heater comprises a tubular heating element and a thermally conductive electrical insulator disposed within the tubular heating element; and passing current through the tubular heating element, thereby causing heating of the resistance heater.

In optional preferred aspects, the method further comprises squeezing the tissue between the two opposing working surfaces. The two opposing working surfaces may preferably be opposite arms or jaws of a pair of tweezers, or a pair of forceps, but need not be limited to such designs.

The present invention also offers advantages not seen in existing resistance wire heating systems that instead incorporate a heating resistance wire covered by an electrically insulating material that is in turn covered by an outer metal sleeve. For example, such existing heaters use an inner resistance wire that is electrically isolated from the outer protective metal sheath. In contrast, the present system uses its outer metal "sheath" as the resistive element. The present invention can thus be used to apply heat more directly to the tissue. A benefit of the present invention is its fast response. Specifically, the present system heats up and cools faster than a resistance wire that is covered by an electrically insulating material that is in turn covered by an outer metal sleeve.

In preferred aspects, the resistance of the tubular heating element is less than the resistance of the surrounding tissues. Thus, current is not passed through the tissue. Instead, the current passes substantially only through the heating element, with the heat generated within the heating element then being transmitted directly to the surrounding tissue by conduction.

DETAILED DESCRIPTION OF THE DRAWINGS

Figure 1:
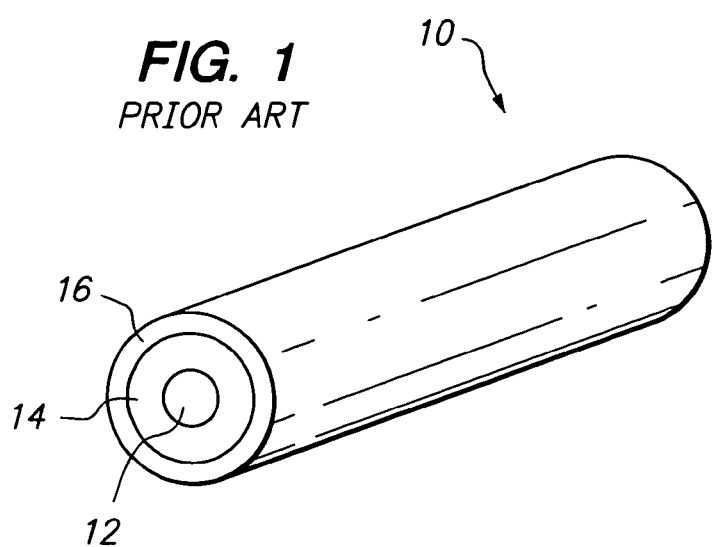
FIG. 1 is a sectional perspective view of a prior art non-medical resistance heater cartridge heating system.

FIG. 1 shows a first prior art resistance wire heater. (Such resistance wire heaters are not used in tissue welding systems.) Heater 10 includes a center resistance heating wire 12. Wire 12 may be made of a resistance alloy such as Nichrome™. Wire 12 is surrounded by a high resistance, electrically insulating, high thermal conductivity core material 14. Core material 14 may be made of a ceramic such as magnesium oxide or boron nitride. Core material 14 is surrounded by an outer metal sheath 16. Metal sheath 16 may be made from stainless steel.

Heater 10 operates with wire 12 carrying electrical current therethrough and with outer metal sheath 16 being electrically insulated from wire 12. A disadvantage of this system is its slow response (i.e., it is both slow to heat up and slow to cool down, thus making it unsuitable for use in a tissue welding device).

Figure 2:
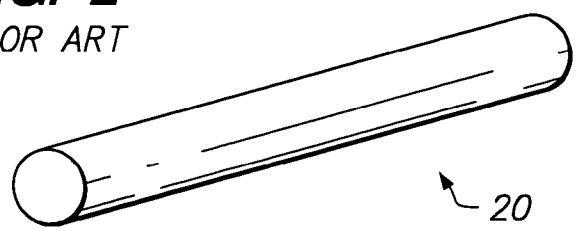
FIG. 2 is a sectional perspective view of a second prior art heating system.

FIG. 2 shows a second prior art heater for use in a tissue welding device. Heater 20 simply comprises a solid resistance alloy wire element as incorporated into the TLS™ Thermal Ligating Shears device sold by Starion Instruments Corporation. The resistance of heater wire 20 is less than the resistance of the surrounding tissue. Therefore, heater wire 20 may be placed in direct contact with surrounding tissue with the tissue being heated with only minimal amounts of electrical current passing through the tissue. An advantage of the heater 20 over heater 10 is its simplicity. Unfortunately, a disadvantage of heater 20 is its small diameter (and thus its small tissue contact surface area) and its small amount of heat transferability.

Figure 3:
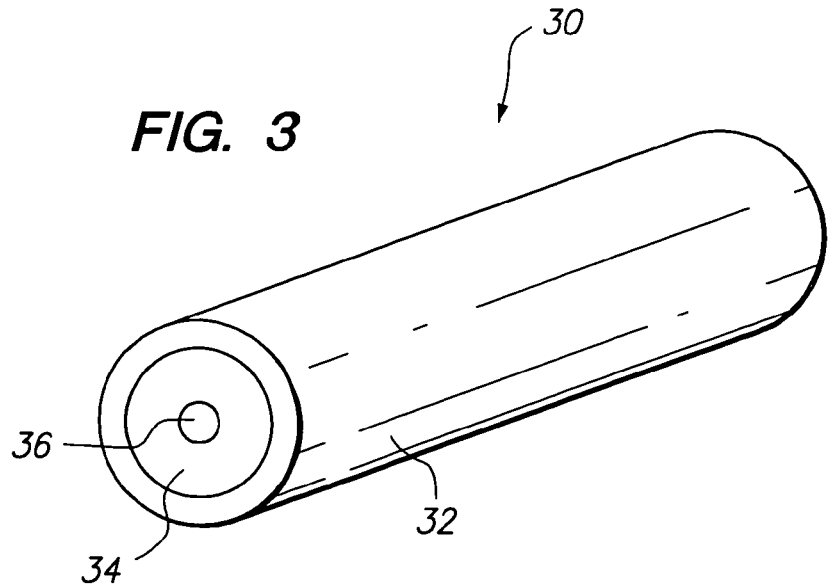
FIG. 3 is a sectional perspective view of a heating element system in accordance with the present invention.

FIG. 3 illustrates a heater 30 in accordance with the present invention. Heater 30 comprises a tubular shaped resistance heating element 32 as its exterior surface. Heating element 32 may be made of any suitable resistance material, including, but not limited to, metal alloys such as Nichrome™ or Inconel™. Within the interior of heating element 32 is disposed a high resistance, electrically insulating, high thermal conductivity core material 34. Core material 34 may be made of a ceramic, and may include materials such as magnesium oxide, boron nitride or aluminum nitride. In optional preferred aspects, core material 34 may simply comprise air or any other gas. In optional aspects of the invention, heater 30 may be formed by metalizing a ceramic rod.

Figure 3A:
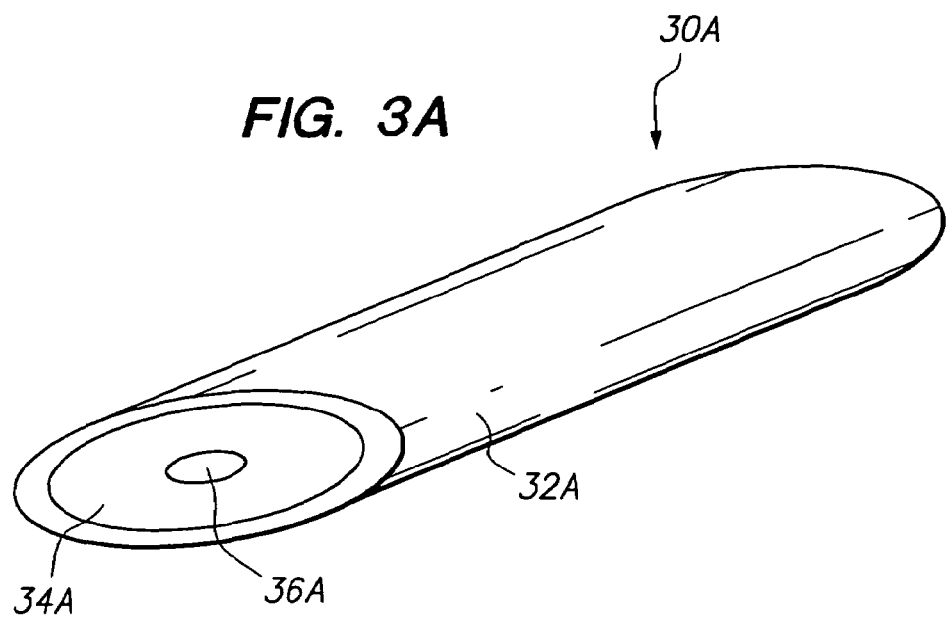
FIG. 3A is a sectional perspective view of an oval shaped heating element system in accordance with the present invention.

FIG. 3A shows an oval shaped embodiment of the invention, which offers the advantage of increased tissue contact surface area (as compared to the embodiment of FIG. 3). Elements 30A, 32A, 34A and 36A in FIG. 3A correspond respectively to elements 30, 32, 34 and 36 in FIG. 3.

In optional aspects of the present invention, a temperature sensing element 36 may also be included. It is to be understood that temperature sensing element 36 is not a critical aspect of the invention, and it may or may not be present, as desired. In various embodiments, temperature sensing element 36 may include a thermocouple, a thermistor, a positive temperature coefficient ("PTC") element or a negative temperature coefficient (NTC) element. A PTC material such as tungsten wire may be especially useful as it may be incorporated within the heater element 32 during manufacturing. Other suitable PTC materials include alloy 120 and iron.

In various preferred embodiments of the present invention, the DC resistance of tubular shaped heating element 32 will be less than that of the surrounding body tissue. More particularly, the resistance of tubular shaped heating element 32 will be less than 10 ohms.

In various preferred embodiments of the present invention, the outer diameter of tubular heating element 32 is between 0.35 mm and 0.55 mm, and the wall thickness is about 0.001 inch.

Figure 5:
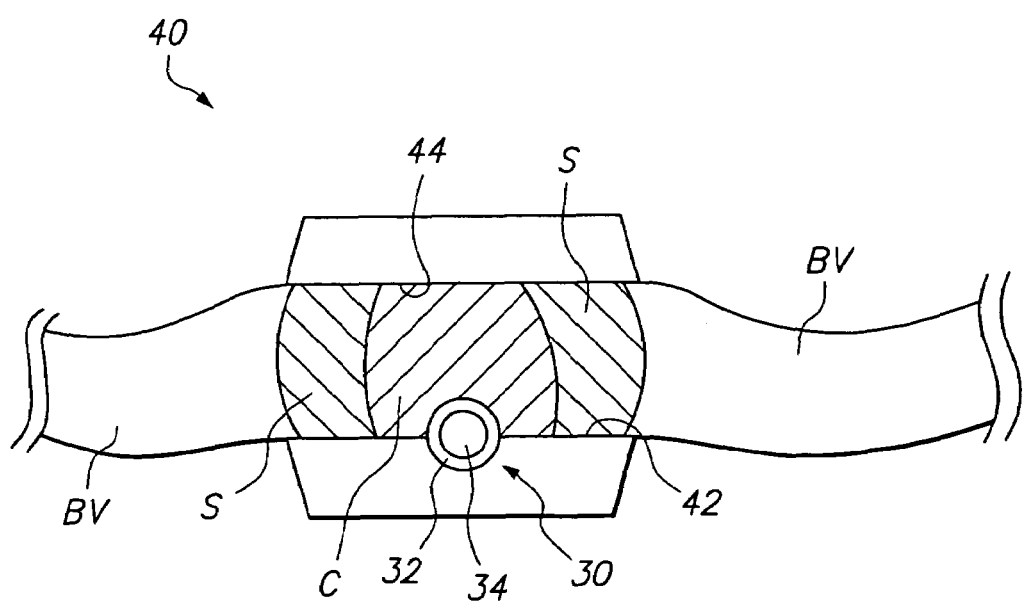
FIG. 5 is a schematic sectional front elevation view corresponding to FIG. 4, showing tissue sealing and cutting zones.
Figure 4:
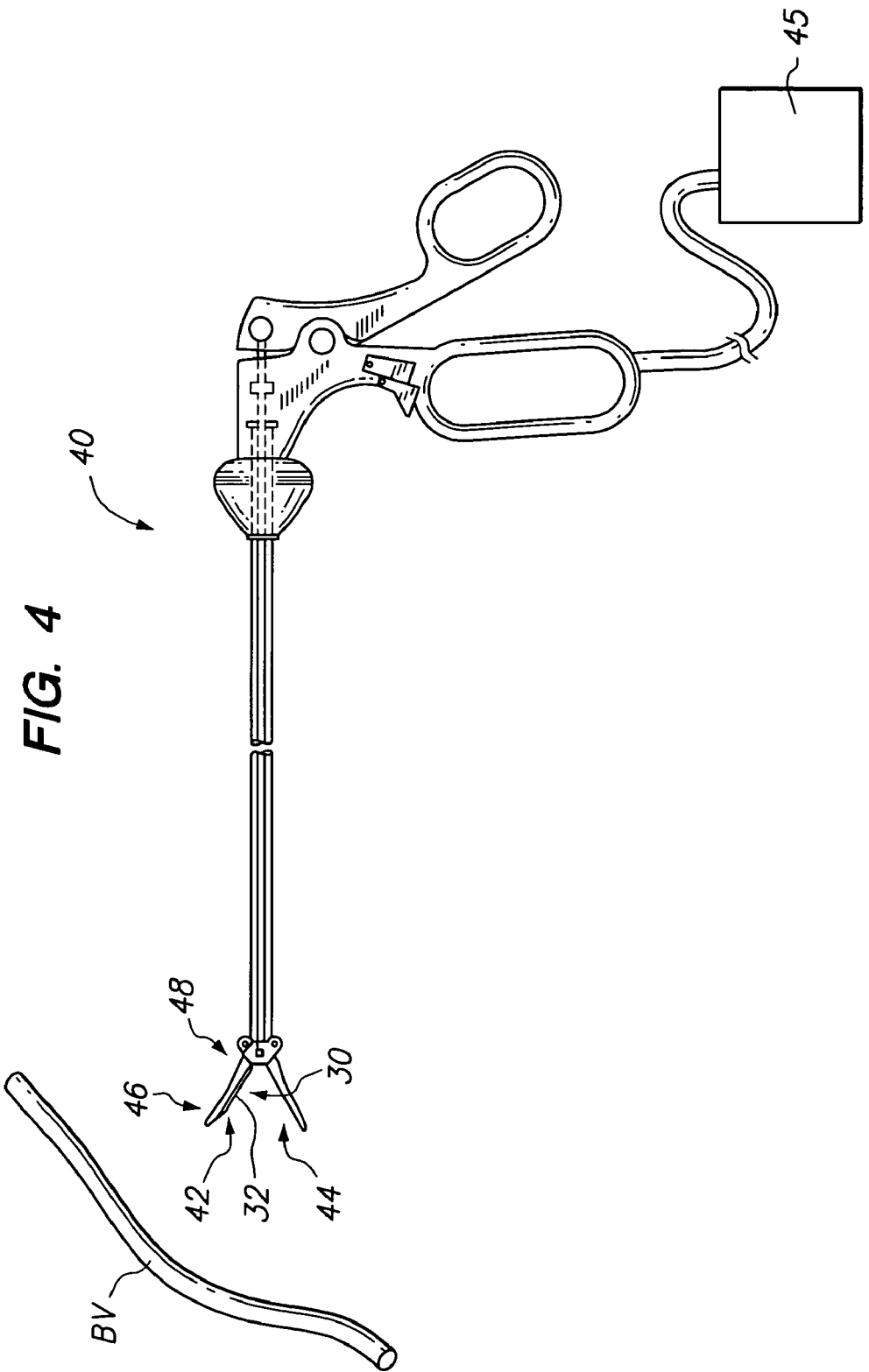
FIG. 4 is a sectional perspective view of the heating element system of FIG. 3 or 3A used on a tissue welding device comprising a pair of tissue grasping tweezers.

The operation of heater 30 of FIG. 3 is illustrated in FIGS. 4 and 5. Referring to FIG. 4, a tissue welding device 40 is provided. Tissue welding device 40 may comprise a pair of ligating shears (as shown) or it may alternately comprise a pair of tweezers or forceps, or any other device adapted to grasp onto and hold tissue between a pair of arms or jaws.

Tissue welding device 40 includes a pair of opposing working surfaces 42 and 44. Heater 30 is positioned on the surface of one or more of the working surfaces. Here, heater 30 is shown positioned on the surface of working surface 42.

In accordance with the novel method of the present invention, tissue welding device 40 is used to cut or seal tissue by first grasping the tissue between two opposing working surfaces 42 and 44; and passing current through the tubular heating element 32, thereby causing heating of the tissue surrounding heater 30. In preferred aspects, the method further includes mechanically squeezing the tissue between opposing working surfaces 42 and 44 while current is passing through tubular heating element 32, so as to better "seal" adjacent tissues together.

Tissue welding device 40 may further include electrical leads 46 and 48 connected to tubular heating element 32 at different points along its length. A power source 45 is electrically connected to leads 46 and 48 so as to conduct current through tubular heating element 32, thereby heating tubular heating element 32. Most preferably, the current passing through tubular heating element 32 will not exceed 10A. Power source 45 may alternately be a constant current power source, a constant voltage power source or a temperature feedback control power source.

FIG. 4 also shows a blood vessel, BV, which can be grasped onto as shown in the schematic view of FIG. 5. As seen in FIG. 5, blood vessel BV is held between working surfaces 42 and 44 of tissue welding device 40. As can be seen, the portion of tissue closest to heater 30 will be heated in excess of 100 degrees Celsius such that the tissue structure is broken down, forming a "cut" zone C. On either side of "cut" zone C, where the tissue is farther away from heater 30, the tissue will only be heated to a temperature between 50 and 90 degrees Celsius, thus forming a "seal" zone S. The mechanical pressure exerted by forcing working surfaces 42 and 44 together against blood vessel BV will further assist in tissue sealing.

What is claimed is:

1. A system for sealing and cutting tissue, comprising:
a body comprising a pair of opposing working surfaces that may be moved together and apart so as to apply pressure to tissue there between; and
a resistance heater disposed on at least one of the working surfaces, wherein the resistance heater comprises a tubular heating element adapted to conduct current therethrough and a thermally conductive electrical insulator disposed within the tubular heating element, wherein the tubular heating element has a resistance of less than 10 ohms when a current of less than 10 amperes passes therethrough, and wherein the working surfaces are dimensioned to apply pressure to tissue in a cutting zone adjacent to the resistance heater while simultaneously applying pressure to tissue in a sealing zone on either side of the cutting zone, wherein the resistance heater and the opposing working surfaces are dimensioned such that the tissue in the cutting zone is in contact with the resistance heater and the tissue in the sealing zones is not in contact with the resistance heater, such that the tissue in the cutting zone can be heated to temperatures in excess of 100 degrees Celsius concurrently with the tissue in the sealing zones being heated to temperatures between 50 to 90 degrees Celsius, and wherein the body does not comprise a moveable blade for slicing through tissue.

2. The system of claim 1, wherein the tubular heating element comprises a metal alloy.

3. The system of claim 1, wherein the thermally conductive electrical insulator comprises a ceramic.

4. The system of claim 3, wherein the thermally conductive electrical insulator comprises magnesium oxide.

5. The system of claim 3, wherein the thermally conductive electrical insulator comprises boron nitride.

6. The system of claim 3, wherein the thermally conductive electrical insulator comprises aluminum nitride.

7. The resistance heater of claim 1, wherein the resistance of the tubular heating element is less than the resistance of surrounding body tissue.

8. The resistance heater of claim 7, wherein the tubular heating element has a DC resistance of less than 10 ohms.

9. The resistance heater of claim 1, wherein the heater is formed by metalizing a ceramic rod.

10. The system of claim 1, further comprising: a temperature sensing element disposed within the thermally conductive electrical insulator.

11. The system of claim 10, wherein the temperature sensing element is selected from the group consisting of a thermocouple, a thermistor, a PTC element and an NTC element.

12. The system of claim 1, wherein the body comprising a pair of opposing working surfaces is a pair of tweezers.

13. The system of claim 1, wherein the body comprising a pair of opposing working surfaces is a pair of forceps.

14. The system of claim 1, further comprising:
a pair of leads connected to the tubular heating element at different points along the length of the tubular heating element so as to conduct current through a length of the tubular heating element.

15. The system of claim 14, further comprising: a power source connected to the pair of leads so as to conduct current through a length of the tubular heating element.

16. The system of claim 1, wherein the thermally conductive electrical insulator comprises a gas.

17. The system of claim 16, wherein the gas is air.

18. The resistance heater of claim 1, wherein the resistance heater is oval-shaped.

19. A method of cutting or sealing tissue with a thermal tissue welding device, comprising:
grasping the tissue between two opposing working surfaces of the thermal tissue welding device, wherein a resistance heater is disposed on at least one of the working surfaces, and wherein the resistance heater comprises a tubular heating element having a resistance of less than 10 ohms and a thermally conductive electrical insulator disposed within the tubular heating element; and
passing a current of less than 10 amperes through the tubular heating element, thereby causing heating of the resistance heater, thereby heating tissue to a cutting temperature in a cutting zone adjacent to the resistance heater, and heating tissue to a sealing temperature in sealing zones on either side of the resistance heater, while simultaneously applying pressure to tissue in the cutting and sealing zones, and wherein the tissue is not sliced by movement of a mechanical blade.

20. The method of claim 19, further comprising: applying pressure to the tissue between the two opposing working surfaces.

21. The method of claim 19, wherein grasping the tissue between the two opposing working surfaces comprises: grasping the tissue with a pair of tweezers.

22. The method of claim 19, wherein grasping the tissue between the two opposing working surfaces comprises: grasping the tissue with a pair of forceps.

23. The method of claim 19, wherein the current passing through the tubular heating element does not exceed 10 A.

24. The method of claim 19, wherein the watt density of the tubular heating element is between 50 W and 800 W per square inch.

25. The method of claim 19, wherein the tissue is heated to a temperature between 50 and 90 degrees Celsius to thereby seal the tissue.

26. The method of claim 19, wherein the tissue is heated to a temperature above 100 degrees Celsius to thereby cut the tissue.

27. The method of claim 19, wherein the method is performed in a constant current mode.

28. The method of claim 19, wherein the method is performed in a constant voltage mode.

29. The method of claim 19, wherein the method is performed in a temperature control feedback mode.

30. The resistance heater of claim 19, wherein the resistance heater is oval-shaped.

\* \* \* \* \*